United States Patent
Lazzara et al.

[19]

[11] Patent Number: 5,863,201
[45] Date of Patent: Jan. 26, 1999

[54] INFECTION-BLOCKING DENTAL IMPLANT

[75] Inventors: Richard J. Lazzara, Lake Worth; Thomas S. Heylmun, West Palm Beach; Keith D. Beaty, Jupiter, all of Fla.

[73] Assignee: Implant Innovations, Inc., Palm Beach Gardens, Fla.

[21] Appl. No.: 778,503

[22] Filed: Jan. 3, 1997

Related U.S. Application Data

[63] Continuation-in-part of Ser. No. 607,903, Feb. 27, 1996, abandoned, which is a continuation-in-part of Ser. No. 351,214, Nov. 30, 1994, abandoned.

[60] Provisional application No. 60/009,592 Jan. 4, 1996.

[51] Int. Cl.$^6$ ..................................................... A61C 8/00
[52] U.S. Cl. .................. 433/201.1; 433/173; 433/199.1; 623/16
[58] Field of Search ........................... 623/16; 433/201.1, 433/199.1, 173, 174

[56] References Cited

U.S. PATENT DOCUMENTS

| | | | |
|---|---|---|---|
| 3,855,638 | 12/1974 | Pilliar | 3/1 |
| 4,145,764 | 3/1979 | Suzuki et al. | 3/1.9 |
| 4,195,409 | 4/1980 | Child | 433/175 |
| 4,547,157 | 10/1985 | Driskell | 433/173 |
| 4,722,688 | 2/1988 | Lonca | 433/173 |
| 4,818,559 | 4/1989 | Hama et al. | 623/11 |
| 4,826,434 | 5/1989 | Krueger | 433/174 |
| 4,874,434 | 10/1989 | Riggs, Jr. | 134/3 |
| 4,908,030 | 3/1990 | Linkow et al. | 623/16 |
| 4,911,953 | 3/1990 | Hosonuma et al. | 427/224 |
| 4,944,754 | 7/1990 | Linkow et al. | 623/16 |
| 5,000,685 | 3/1991 | Brajnovic | 433/173 |
| 5,030,096 | 7/1991 | Hurson et al. | 433/173 |
| 5,071,351 | 12/1991 | Green et al. | 422/23 |
| 5,188,800 | 2/1993 | Green et al. | 433/173 |

(List continued on next page.)

FOREIGN PATENT DOCUMENTS

| | | |
|---|---|---|
| 606566 A1 | 7/1994 | European Pat. Off. . |
| 679117 A5 | 12/1991 | Switzerland . |
| 2252501 | 8/1992 | United Kingdom . |

OTHER PUBLICATIONS

Baier, R.E; A.E. Meyer "Implant Surface Preparation," *International Journal of Oral & Maxillofacial Implants*, vol. 3, 9–20, 1988.

Binon, P. "Evaluation of Machining Accuracy and Consistency of Selected Implants, Standard Abutments, and Laboratory Analogs," *The International Journal of Prosthodontics*, vol. 8, 162–178, 1995.

Bowers, K.; Keller, J.; Randolph, B.; Wick, D.; Michaels, C. "Optimization of Surface Micromorphology for Enhanced Osteoblast Responses In Vitro" *International Journal of Oral & Maxillofacial Implants*. vol. 7 No. 3, pp.302–310, 1992.

Branemark, P.I.; B.O. Hansson; R. Adell; U. Breine; J. Lindstrom; O. Hallen; A. Ohman *Osseointegrated implants in the Treatment of the Edentulous Jaw Experience from a 10–year period*, Stockholm, Almqvist & Wiksell International, 1977.

Buser, D.; R.K. Schenk; S. Steinemann; J.P. Fiorellini; C.H. Fox; and H. Stich "Influence of Surface Characteristics on Bone Integration of Titanium Implants. A Histomorphometric Study in Miniature Pigs" *Journal of Biomedical Materials Research*, 25, 889–902, 1991.

(List continued on next page.)

*Primary Examiner*—Paul B. Prebilic
*Attorney, Agent, or Firm*—Arnold White & Durkee

[57] ABSTRACT

An infection-blocking dental implant in which a threaded portion which contacts bone is roughened except for up to three threads which may be exposed by bone recession after implantation, which have a smooth surface. Preferably, the implant is of titanium or titanium alloy and the threaded portion is roughened by a two-step acid treatment.

12 Claims, 1 Drawing Sheet

U.S. PATENT DOCUMENTS

| | | | |
|---|---|---|---|
| 5,190,795 | 3/1993 | Culler | 427/226 |
| 5,205,745 | 4/1993 | Kamiya . | |
| 5,297,963 | 3/1994 | Dafatry | 433/172 |
| 5,316,476 | 5/1994 | Krauser | 433/173 |
| 5,316,477 | 5/1994 | Calderon | 433/173 |
| 5,344,425 | 9/1994 | Sawyer | 606/198 |
| 5,344,457 | 9/1994 | Pilliar et al. | 623/16 |
| 5,360,448 | 11/1994 | Thramann | 623/16 |
| 5,362,237 | 11/1994 | Chalifoux | 433/220 |
| 5,368,480 | 11/1994 | Balfour et al. | 433/141 |
| 5,368,483 | 11/1994 | Sutter et al. | 433/173 |
| 5,399,090 | 3/1995 | Padros-Fradera | 433/173 |
| 5,433,606 | 7/1995 | Niznick et al. | 433/173 |
| 5,456,723 | 10/1995 | Steinemann et al. | 623/16 |
| 5,478,237 | 12/1995 | Ishizaswa | 433/201.1 |
| 5,489,210 | 2/1996 | Hanosh | 433/173 |
| 5,503,558 | 4/1996 | Clokie | 433/173 |
| 5,564,923 | 10/1996 | Grassi et al. | 433/173 |
| 5,571,017 | 11/1996 | Niznick | 433/174 |
| 5,573,401 | 11/1996 | Davidson et al. | 433/201.1 |
| 5,588,838 | 12/1996 | Hansson et al. | 433/174 |
| 5,603,338 | 2/1997 | Beaty | 623/16 |

OTHER PUBLICATIONS

Carlsson, L.; T. Rostlund; B. Albrektsson; T. Albrektsson "Removal Torques for Polished and Rough Titanium Implants," *International Journal of Oral & Maxillofacial Implants*, vol. 3, 21–24, 1988.

Cook, S.; F. Georgette; H. Skinner; R. Haddad, Jr. "Fatigue properties of carbon–and porous–coated Ti–6Al–4V alloy," *Journal of Biomedical Materials Research*, vol. 18, 497–512, 1984.

Curtis, A.S.G. and Clark, Peter "The Effects of Topographic and Mechanical Properties of Materials on Cell Behavior," *Critical Reviews in Biocompatibility*, vol. 5, Issue 4, 343–362, 1990.

de Groot, K.; R. Geesink; C. Klein; P. Serekian "Plasma sprayed coatings of hydroxylapatite," *Journal of Biomedical Materials Research*, vol. 21, 1375–1381, 1987.

Eberhardt, A.; B. Kim; E. Rigney; G. Kutner; C. Harte Effects of Precoating Surface Treatments on Fatigue of Ti–6Al–4V, *Journal of Applied Biomaterials* vol. 6, 171–174, 1995.

Ingemar Olefjord; S. Hansson "Surface Analysis of Four Dental Implant Systems" *International Journal of Oral & Maxillofacial Implants*, vol. 8, No. 1, 32–40, 1993.

Kasemo, B.; J. Lausmaa "Metal Selection and Surface Characteristics," *Tissue–Integrated Prostheses Osseointegration in Clinical Dentistry* (Quintessence Books) 99–116, 1985.

Klokkevold, P.; and Adachi, M. "Evaluation of a New Chemically Enhanced Implant Surface by Torque Removal Tests in the Rabbit Femur," UCLA School of Dentistry, Section of Periodontics, Los Angeles, CA, 1996, Accepted for publication in *Clinical Oral Implants Research* (1997).

Lazzara, R.; A.A. Siddiqui; P. Binon; S. Feldman; R. Weiner; R. M. Phillips; A. Gonshor "Retrospective Multicenter Analysis of 3i Endosseous Dental Implants Placed Over a Five–Year Period," *Clinical Oral Implants Research* 1996: 7: 73–83.

Messersmith, P.; F. Cooke "Stress enhancement and fatigue susceptibility of porous coated Ti–6A1–4V implants: an elastic analysis," *Journal of Biomedical Materials Research*, vol. 24, 591–604, 1990.

Predecki, Paul; B.A. Auslaender; J.E. Stephan; Vert L. Mooney; Carl Stanitski "Attachment of Bone to Threaded Implants by Ingrowth and Mechanical Interlocking," *J. Biomed. Mater. Res.* vol. 6, 401–412, 1972.

Schulte, J.; "External Hex Manufacturing Tolerances of Six Implant Systems: A Pilot Study," *Implant Dentistry*, 51–53, Spring 1994.

Sorensen, J.; S. Avera; C. Thomas "Comparison of Interface Fidelity of Implant Systems," *Journal of Dental Research*, vol. 70, No. 540, Abstract No. 2191, 1991.

Sullivan DDS, Daniel; Richard L. Sherwood DDS; Tiffany N. Mai DDS, "Preliminary Results of a Multicenter Study Evaluating Chemically–Enhanced Pure Titanium Implants," Accepted for publication in the *Journal of Prosthetic Dentistry*, 1997.

Thomas, K.A.; J.F. Kay; S.D. Cook; M. Jarcho "The effect of surface macrotexture and hydroxylapatite coating on the mechanical strengths and histologic profiles of titanium implant materials," *Journal of Biomedical Materials Research*, vol. 21, 1395–1414, 1987.

Weinlaender, M.; Kenney, E.B.; Lekovic, V.; Beumer, J.; Moy, P.; Lewis, S.; "Histomorphometry of Bone Apposition Around Three Types of Endosseous Dental Implants," *International Journal of Oral and Maxillofacial Implants*, vol. 7, No. 4, 491–496, 1992.

Wennerberg, A.; Albrektsson, T.; Andersson, B.; "Design and Surface Characteristics of 13 Commercially Available Oral Implant Systems," *International Journal of Oral & Maxillofacial Implants*, vol. 8, No. 6, 622–633, 1993.

Wheeler DDS, Stephen L. "Eight–Year Clinical Retrospective Study of Titanium Plasma–Sprayed and Hydroxyapatite–Coated Cylinder Implants," *International Journal of Oral and Maxillofacial Implants*, vol. 11, No. 3, 340–350, 1996.

Wilke, H.J.; L. Claes; S. Steinemann; "The Influence of Various Titanium Surfaces on the Interface Shear Strength Between Implants and Bone," *Advances in Biomaterials*, 9, 309–314 Elsevier Science Publishers B.V., Amsterdam, 1990.

Wong, M.; J. Eulenberger; R. Schenk; and E. Hunziker; "Effect of Surface Topology on the Osseointegration of Implant Materials in Trabecular Bone," *Journal of Biomedical Materials Research* 29, 1567–1575, 1995.

Yue, S.; R. Pilliar; G. Weatherly "The fatigue strength of porous–coated Ti–6%Al–4%V implant alloy," *Journal of Biomedical Materials Research*, vol. 18, 1043–1058, 1984.

Sutter et al., *The New Restorative Cocnept of the ITI Dental Implant System: Design and Engineering*; vol. 13, No. 5, pp. 408–413, 1993.

Ledermann et al., *The Ha–TI Implant*, Schweiz Monatsschr Zahnmed, vol. 101:5/1991 (7 pages).

"Ion–Beam–Sputter Modification of the Surface Morphology of Biological Implants," *J. Vac. Soc. Technol.*, vol. 14, No. 1, Jan./Feb. 1977, pp. 326–331.

"The Influence of Various Titanium Surfaces On the Interface Strength between Implants and Bone " *Advances in Biomaterials*, vol. 9, pp. 309–314, Elsevier Science Publishers BV, Amsterdam, 1990.

"Influence of Surface Characteristics on Bone Integration of Titanium Implants," *Journal of Biomedical Materials Research*, vol. 25, pp. 889–902, John Wiley & Sons, Inc., 1991.

"Short–term Plasma–cleaning Treatments Enhance In Vitro Osteoblast Attachment to Titanium," *Journal of Oral Implantology*, vol. XVIII, No. 2 (1992), pp. 130–137.

"Design and Surface Characteristics of 13 Commercially Available Oral Implant Systems," *Int. J. Oral Maxillofactial Implants*, 1993, 8:622–633.

Albrektsson, T., P.I. Branemark, H.A. Hansson & J. Lindstrom, "Osseointegrated Titanium Implants," 1991.

"Step–Screw Implant," *Dental Products Report*, Mar. 1993.

Baier, R. E., et al., "Surface Energetics And Biological Adhesion," International Symposium on Physiocochemical Aspects of Polymer Surfaces, vol. 2, pp. 895–909.

Shultz, R. R., et al., "*A Study Of Fatigue Properties Of Hydroxylapatite Coated Titanium Alloy Implant Materials*," Department of Biomedical Engineering, Memphis State University.

Tarnow, Dennis P., DDS, "*Dental Implants In Periodontal Care*," Current Science, 1993, pp. 157–162.

INFECTION-BLOCKING DENTAL IMPLANT

The present application is a continuation-in-part of Ser No. 08/607,903 filed Feb. 27, 1996, now abandoned, which is a continuation-in-part of Ser. No. 08/351,214 filed Nov. 30, 1994 which is now abandoned. The present application also claims priority to provisional application Ser. No. 60/009,592 filed Jan. 4, 1996.

FIELD OF THE INVENTION

This invention relates to dental implants intended for insertion in a hole provided in living jawbone for eventual support of artificial teeth. It is illustrated as realized in a cylindrical dental implant having a screw thread or screw threads on its outer surface, but it is not limited to that type of implant, and is applicable to all types of implants which share the general characteristic that while they are fitted into the living jawbone they extend out of it through the overlying gingival into the mouth wherein they support artificial teeth.

BACKGROUND OF THE INVENTION

The part of a dental implant that is in the living jawbone should have a roughened surface confronting the host bone for bonding with the bone, and the part of the same implant that is exposed in the mouth should have a smooth surface because a rough surface in that location might provide a site where bacteria can attach and proliferate. For hygienic reasons the exposed surfaces of the implant should be smooth, while for osseointegration purposes the surfaces of the implant confronting the host bone should be rough. Experience over many years has taught dentists practicing implantology that approximately eighteen months after an implant has been successfully placed in the jawbone of a patient and is performing its task of supporting artificial dentition, the bone surrounding the implant immediately beneath the overlying gingival tissue will in most cases be found to have receded a small distance, exposing to the soft tissue a portion of the roughened surface of the implant which had been in bone. This phenomenon is illustrated in a book by Branemark, Zarb & Albrektsson entitled "Tissue-Integrated Prostheses" 1985, p56, FIG. 1–46. This event, occurring as it does beneath the gum tissue surrounding an artificial tooth, is not immediately visible. In spite of the most diligent hygienic practice, it presents the danger that bacteria which succeed in penetrating between the tooth and its surrounding tissue may attach themselves to the roughened surface, and there proliferate, and bring about an infection putting the implant and the tooth it supports in danger of failure.

In U.S. Pat. No. 4,988,299 an implant is disclosed which has a threaded portion and a smooth neck portion. No reference is made to roughening of the threaded portion or how smooth the neck portion should be. The neck portion is defined by having a diameter between the "core" diameter of the threaded portion and the outer diameter of the threads and it is disclosed to have a curved surface. The neck portion is said to have an axial length exceeding the settlement in bone level and it is intended to avoid exposure of the threads.

SUMMARY OF THE INVENTION

The present invention relates to an implant which is roughened to improve osseointegration with the bone but which does not provide a surface which can facilitate infection.

Observations based on practical experience of one of the present inventors over the past ten years or more have revealed that the recession described in the above-mentioned book tends to stop at the level where the implant places a load on the host bone. In a screw-type implant this level is approximately the beginning of the first turn of the screw thread near the gingival end of the implant. However, these observations also indicate that the stopping level is not precisely the same in all cases, and that in some cases the first thread may be exposed. At times, more than one thread is exposed, perhaps up to three threads.

According to the invention as illustrated in the accompanying drawings, the portion of the implant which has a roughened surface is limited to that portion which can be expected to remain in contact with the host bone after the expected bone recession has taken place. The head portion of the implant and the immediately-adjacent part of the heretofore roughened portion, including the initial part of the screw threads, are made smooth. Preferably one to three threads will be left smooth, not roughened. Typically, a length of about 3 mm below the top surface of the implant will be left smooth and not roughened with the remainder of the implant. Because the amount of bone that recedes will vary with different patients, one or more smooth threads may remain permanently in the bone along with the roughened threads. Although these smooth threads may not load the bone to the same degree as the roughened threads, nevertheless the smooth threads will still add significantly to the bone loading.

Since the exact amount of bone recession that will occur in a given patient cannot be determined in advance of the event with precision, the invention is useful to minimize the danger of infection from this source, that is, to block the infection. Good hygienic practice will continue to be required of the patient. With the invention, such good practice can be expected to be more fruitful than heretofore.

BRIEF DESCRIPTION OF THE DRAWINGS

The invention is described in greater detail with reference to the accompanying drawings, in which.

DETAILED DESCRIPTION OF THE INVENTION

Figure 2:
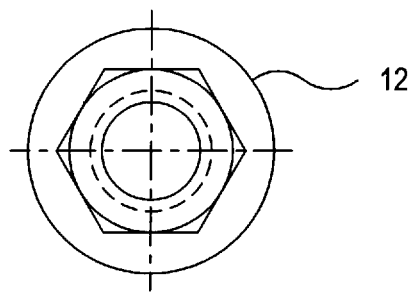
FIG. 2 is an end view of the dental implant of FIG. 1.

The implant 10 has a head portion 12, a neck portion 14 and a main body 16 which is roughened on its outer surface in the region 18. Such implants are normally machined a titanium alloy and are smooth, until a portion is roughened to facilitate with bone. The head portion 12, the neck portion 14, and a small region ody 16 immediately adjacent the neck portion, encompassing the first to third thread turns, are smooth. To achieve this result the portions of the implant intended to remain smooth during and after the roughening procedure may be covered during that procedure. For example, if the roughening procedure includes an acid-etching step or steps, these parts may be covered with a suitable wax prior to immersing the implant in the etching acid. A preferred method of roughening the surface is disclosed in copending U.S. patent application Ser. No. 08/607,903 mentioned above and incorporated by reference herein. The process has two steps, the first being removal of native oxide from titanium by contact with an aqueous hydrofluoric acid solution, followed by etching with a mixture of sulfuric and hydrochloric acids.

Figure 1:
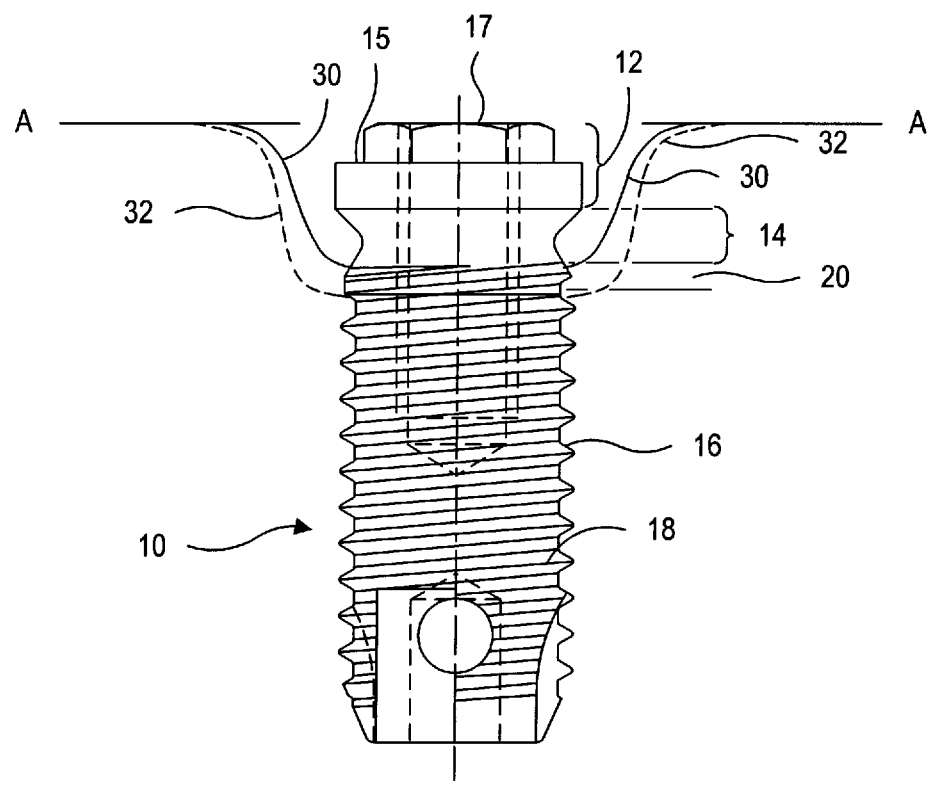
FIG. 1 is a side elevation of a dental implant according to the invention.

When the implant 10 is first installed in a bore prepared for it in a patient's jawbone, the implant is buried in bone up to and including the head portion 12, to the level indicated by line A—A in FIG. 1. The healing phase then begins, during which new bone is formed close to the immobile, resting implant, and the implant will remain buried in the bone, up to the head portion. All the implant, including the neck portion 14, will confront the host bone in the early part of the healing phase. Thereafter when the implant is loaded and the remodeling phase begins (overlapping the healing phase) during exposure to masticatory forces, the newly formed bone remodels under the applied load until, after about eighteen months, a steady state is achieved. In this state the anchoring bone will be found to have undergone a reduction in height (bone recession) immediately adjacent the implant. The amount of this recession can vary from case to case, between the level indicated by the solid curved lines 30 and the level indicated by the broken curved lines 32, for example, exposing the head portion 12, the neck portion 14 and some or all of the immediately adjacent region 20 of the threaded main body 16. In some cases region 20 may extend further, up to about the third thread. Another way to define regions 14 and 20 is that roughening of the implant begins about 3 mm below the upper flat surface 15 of the implant 10, which receives connecting parts of the dental restoration.

According to the invention, that region 20 immediately adjacent to the neck portion 14 of the implant is maintained smooth so that when the remodeling phase is completed, there will be little or no roughened implant surface exposed to the soft tissue under the dental restoration that is supported on the implant. The exact dimensions of the smooth region 20 cannot be precisely established for all cases. A length corresponding to about one turn of the screw thread is suitable for many cases, but up to three threads may be left smooth.

We claim:

1. A dental implant having a head portion, a neck portion, and a threaded portion for contact with bone wherein said head and neck portions are provided with a smooth surface for contact with overlying gingival tissue for blocking infection and said threaded portion is roughened to promote osseointegration with bone while leaving at least one thread adjacent said neck portion smooth and unroughened, wherein said implant is titanium or a titanium alloy and said roughness is created by a two-step process in which the native oxide is removed by contact with a first acid solution and followed by etching of the resulting surface with a second acid solution.

2. A dental implant of claim 1 wherein up to three threads adjacent said neck portion are left smooth.

3. A dental implant of claim 1 wherein a length of about 3 mm of said implant including said head, neck, and adjacent threaded portions is left smooth.

4. A dental implant of claim 1 wherein the head, neck, and threaded portions left smooth have a surface created by machining.

5. A dental implant comprising
   (a) a roughened bottom portion for facilitating osseointegration with bone;
   (b) a smooth neck portion adjacent said roughened portion for contact with gingival tissue; and
   (c) a smooth head portion adjacent said neck portion for receiving a dental restoration; wherein said roughened portion of (a) is threaded and at least one thread adjacent said neck portion is left smooth and unroughened;
   wherein said implant is titanium or titanium alloy and said roughness is created by a two-step process in which the native oxide is removed by contact with a first acid solution and followed by etching of the resulting surface with a second acid solution.

6. A dental implant of claim 5 wherein up to three threads adjacent said neck portion are left smooth and unroughened.

7. A dental implant of claim 5 wherein the length of said head, neck, and smooth threads is a total of about 3 mm.

8. A dental implant of claim 5 wherein the head, neck, and threaded portions left smooth have a surface created by machining.

9. A dental implant of claim 1 wherein said first acid solution is aqueous hydrofluoric acid.

10. A dental implant of claim 5 wherein said first acid solution is aqueous hydrofluoric acid.

11. A dental implant of claim 9 wherein said second acid solution is a mixture of sulfuric and hydrochloric acids.

12. A dental implant of claim 10 wherein said second acid solution is a mixture of sulfuric and hydrochloric acids.

* * * * *

UNITED STATES PATENT AND TRADEMARK OFFICE
CERTIFICATE OF CORRECTION

PATENT NO. : 5,863,201
DATED : January 26, 1999
INVENTOR(S) : Lazzara et al.

It is certified that error appears in the above-identified patent and that said Letters Patent is hereby corrected as shown below:

<u>Title page,</u>
Item [63], Related U.S. Application Data, before "which," delete "abandoned" and insert -- pending --.

Signed and Sealed this

Fifteenth Day of June, 2004

JON W. DUDAS
*Acting Director of the United States Patent and Trademark Office*